(12) United States Patent
Clemons et al.

(10) Patent No.: US 7,390,091 B2
(45) Date of Patent: Jun. 24, 2008

(54) VISION TESTING APPARATUS

(75) Inventors: Michael Clemons, Manakin Sabot, VA (US); Philip Remedios, Palm Harbor, FL (US)

(73) Assignee: Sperian Protection Optical, Inc., Smithfield, RI (US)

( * ) Notice: Subject to any disclaimer, the term of this patent is extended or adjusted under 35 U.S.C. 154(b) by 260 days.

(21) Appl. No.: 11/118,804

(22) Filed: Apr. 29, 2005

(65) Prior Publication Data

US 2006/0244915 A1   Nov. 2, 2006

(51) Int. Cl.
 A61B 3/00   (2006.01)
 A61B 3/02   (2006.01)

(52) U.S. Cl. .................. 351/245; 351/243; 351/239

(58) Field of Classification Search ......... 351/205–223, 351/239–246
See application file for complete search history.

(56) References Cited

U.S. PATENT DOCUMENTS

| | | | | |
|---|---|---|---|---|
| 4,053,212 | A | 10/1977 | Teichner et al. | 351/243 |
| 4,298,253 | A | 11/1981 | Tagnon | 351/239 |
| 4,412,729 | A | 11/1983 | Hartmann | 351/239 |
| 4,452,515 | A | 6/1984 | Lewis | 351/243 |
| 4,572,629 | A | 2/1986 | Tagnon | 351/243 |
| 4,597,651 | A | 7/1986 | Capo-Gual et al. | 351/243 |
| 4,740,072 | A * | 4/1988 | Griffin et al. | 351/243 |
| 4,786,142 | A | 11/1988 | Karecki | 359/894 |
| 4,844,607 | A | 7/1989 | Andera et al. | 351/243 |
| 5,255,027 | A | 10/1993 | Reiner et al. | 351/211 |
| 5,483,305 | A * | 1/1996 | Kohayakawa | 351/243 |
| 5,485,231 | A | 1/1996 | Hayashi et al. | 351/243 |
| 5,568,209 | A * | 10/1996 | Priester et al. | 351/243 |
| 6,244,713 | B1 | 6/2001 | Hayashi | 351/243 |
| 6,350,032 | B1 * | 2/2002 | Menozzi et al. | 351/239 |

FOREIGN PATENT DOCUMENTS

| | | |
|---|---|---|
| DE | 2939940 | 5/1978 |
| DE | 3241958 | 11/1981 |
| EP | 102887 | 3/1984 |
| EP | 487073 | 11/1990 |
| EP | 578236 | 7/1992 |

OTHER PUBLICATIONS

Brochure or Product Information Sheets for Rodatest 300 and 302 (Date Unknown).

* cited by examiner

*Primary Examiner*—Mohammed Hasan
(74) *Attorney, Agent, or Firm*—Thomas & Raring, P.C.

(57) ABSTRACT

A vision test apparatus includes a viewing assembly connected to a chassis wherein the viewing assembly creates an optical path between an image display and at least one front lens. A near/far assembly includes a secondary lens selectively operable with the front lens to create virtual visual distances. An optional transparent panel intersects the optical path and operates at least partially obscure the image display so that the vision testing apparatus has a means to isolate a portion of the image display. A lifting mechanism is operable to raise or lower the viewing assembly for patients of various heights. The viewing apparatus is also rotatable independently of said chassis to present natural lines of sight to a patient during near and far testing.

28 Claims, 12 Drawing Sheets

VISION TESTING APPARATUS

FIELD OF THE INVENTION

The present invention relates to the field of ophthalmic instruments, and more particularly, to an improved vision tester designed for accurate and precise measurement of visual performance

BACKGROUND OF THE INVENTION

Many types of vision testers are known including those previously described by the present applicant in U.S. Pat. Nos. 6,350,032 and 4,740,072. These disclosures are incorporated by reference herein.

Technology related to healthcare devices and procedures is continuously improving. This constant improvement makes it possible to identify new populations that are underserved by existing technologies and to also assist these newly identified populations. Advances in technology lead to the improvement and modification of existing devices so that new and old healthcare issues can be addressed in more efficient and effective ways.

Vision testing is one healthcare area that benefits greatly from improved technology. Current vision testing devices present an optical path from a front lens to an image display. The image display generally comprising a plurality of rows and columns of varying sizes and/or shapes wherein each row or column presents various characters for the patient to identify. These characters are often found on a rotating disk or test slides mounted on a rotatable drum. The image displays typically require an illumination source as the test characters on the rotating disk, rotatable test slide, or the like are located in light blocking viewing assemblies.

In use, the patient views every row and column and the test administrator specifies the characters or objects that the patient should focus on. While it is often necessary to test small children for vision problems, it is very difficult for children to understand the concept of rows and columns. The party performing the vision test may not be able to adequately explain the procedure or may not be sure the child is properly reading the column or row the tester is indicating. Misdiagnoses and inefficiencies are generated by this confusion.

Even where particular rows or columns are highlighted, the patient must understand concepts such as "left to right" or "top to bottom." This can be difficult to convey to children, mentally handicapped patients, patients that are not fluent in the tester's language, or in other similar circumstances. For instance, certain cultures read left to right while other cultures read from the right to the left, and it is possible for the tester and patient to have a different understanding of how to "read" a highlighted row. Known methods for blocking certain rows and/or columns of the image display include manually adding parts to a vision testing apparatus. Vision testers require more efficient and effective means to test patients.

Vision tests are performed by testing a patient's sight at various simulated distances where "far" or "distance vision" is considered to be approximately 20 feet between the patient and an object and where "near" or "reading vision" is considered to be about 14 inches. Near and far testing can be conducted on known vision testing machines. This has been achieved via a lens, or set of lenses, that simulate the distance to be tested. The near/far lenses can be moved to intersect the optical path provided by the viewing assembly. The vision testing assembly does not move when the tester moves from near to far vision testing and vice-versa. Some vision testing devices use two or more distinct optical paths. This leads to bulky and overly complicated vision testing machines.

It should be understood that the natural line of sight for a person who is reading tends to be at a downward angle as the reading material is below the person's straight-ahead line of sight. As such, bifocals, trifocals and progressive lenses have varying magnification regions along the vertical axis of the lens with magnifications for near distance reading or writing located in the lower portion of the lens. Vision testing devices with only one optical path do not account for patients who have these types of lenses, which is to say that patients look straight into a vision testing device when testing "near" vision. This unnatural line of sight can lead to inaccurate results. Patients with corrective lenses are also inconvenienced by the need to adjust their lenses or head position to account for the unnatural line of sight. Even with multiple optical paths, the arbitrary angle supplied by the vision testing apparatus may not be optimum for a given patient. Moreover, it may be difficult for a patient to find the ideal angle and/or to hold their head or eyewear at that angle. For instance, aged patients may be unable to steadily hold their eyewear at the angle necessary to test the near vision portion of their corrective lenses.

It is also important for vision testing devices to provide portability or a small storage footprint, which is one reason devices with multiple optical paths are not favored as they tend to require more space. Yet, many vision testing machines cannot be collapsed or otherwise condensed and they, therefore, require bulky, hard storage or transport cases. Preferably, a vision testing apparatus would include a storage or transport configuration and a range of raised configurations. The configurations should be effective for patients of various heights.

A vision testing apparatus in accordance with the present invention provides a system for accurately testing vision. The present invention solves long-standing needs by providing a means to highlight and/or isolate portions of a vision test image so that a vision test is more efficiently and effectively administered. The apparatus of the present invention provides a storage/transport configuration and a range of raised configurations, and the apparatus operates in any configuration to serve patients of varying heights. The vision testing apparatus of the present invention also provides a means to rotate the a patient's line of sight without adjusting the apparatus' configuration. The adjustable line of sight mechanism simulates natural line of sight differences for distance and near vision testing.

SUMMARY OF THE INVENTION

In accordance with the present invention, a vision testing apparatus is provided with a lifting mechanism to raise or lower a viewing assembly, the viewing assembly rotatable separately from the lifting mechanism wherein the viewing assembly is operable to obscure at least one character within the viewing assembly to be identified by a patient. The rotatable viewing assembly provides a range of motion independent of the lifting mechanism's position in order to simulate natural line of sight differences between distance and near vision testing. The present invention overcomes the foregoing drawbacks and provides a vision testing apparatus that solves those and other problems.

Specifically, the vision testing apparatus of the present invention is encased by a number of body panels. A support chassis includes a base and sidewalls. The lifting mechanism includes arms connecting the sidewalls to the viewing assembly. The viewing assembly is at least partially enclosed by a viewing housing. The arms rotate through a range of motion between a first storage/transportation configuration and a range of raised configurations (the apparatus operates in any configuration). In a storage configuration, the viewer housing is lowered towards the base to form a compact package. The raised configurations involve raising the viewer housing away from the base along a nearly vertical vector. A height adjustable viewing assembly in accordance with the present invention is effective for patients of differing heights.

In a preferred embodiment, the lifting mechanism includes a lost motion coupling. The lost motion coupling ensures that the angle of the viewing assembly relative to the patient is substantially maintained along the lifting mechanism's range of motion. At the highest raised positions, the viewing assembly may begin to tilt to accommodate the tallest patients. A hydraulic cylinder may also form a part of the lifting mechanism.

The viewing assembly itself comprises a light occluding casing with one or more front lenses. The viewing assembly is mainly located within the viewer housing for aesthetic reasons. The viewing assembly provides an optical path from the front lenses to an image display inside the casing. In use, a patient looks through the front lenses in order to identify characters in the image display.

A near/far assembly is selectively actuated to intersect the optical path between the front lenses and the image display. The near/far assembly can be actuated to include an additional lens or plurality of lenses in the optical path. In a second position, the near/far assembly is positioned so that the optical path includes only the front lens or lenses.

To accommodate patients with corrective eyewear and/or to provide a more natural line of sight, the patient or tester can operate a mechanism located on the viewing assembly that adjusts the angle of the viewing assembly relative to the patient. In one preferred embodiment, this line of sight adjustment mechanism is a rack-and-pinion mechanism. This rack-and-pinion mechanism allows the viewing assembly to be rotated in relation to the chassis so that the patient's viewing angle can be manipulated. This is of particular importance to patients with bifocal, trifocal or progressive lens, but the ability to adjust the viewing angle generally enables a vision test to be administered using a natural line of sight (i.e., downward viewing angle for near vision testing and a straight-ahead viewing angle for far vision testing). The natural line of sight is achieved while the apparatus uses only a single optical path.

In another preferred embodiment, the viewing assembly includes at least one transparent panel that intersects the optical path. The panel can be operated to partially block or shade the image display.

In a preferred embodiment of the transparent panel, the panel includes a number of pixels that can be individually activated. In an activated state, the individual pixels are operable to shade or block light passing through that portion of the panel. In an unactivated state, light passes through the panel at that pixel without any shading noticeable to the patient. This embodiment of the present invention, therefore, allows a tester to selectively activate pixels so that individual characters on a test slide are highlighted or isolated via a tester-operated control board, remote control, or the like. The panel can be operated so as to allow only one object, a row of objects, or a column of objects to be unobscured or visible to the patient. Characters to be ignored appear to be shaded or are not visible to the patient. The character or characters to be viewed by the patient would effectively be highlighted. It is also possible to deactivate each pixel so that all the objects or characters are equally visible.

BRIEF DESCRIPTION OF THE DRAWINGS

The foregoing, and additional objects, features, and advantages of the present invention will become apparent to those of skill in the art from the following detailed description of a preferred embodiment thereof, taken in conjunction with the accompanying drawings, in which.

DETAILED DESCRIPTION OF A PREFERRED EMBODIMENT

The invention will be described in the context of one or more preferred embodiments. FIGS. 1-13 illustrate a vision testing apparatus in accordance with preferred embodiments of the present invention, but it is to be understood that an engineer or designer having ordinary skill in the art of vision testing apparatus assembly will be able to create a vision testing apparatus that incorporates the teachings of the present invention but which may look different and incorporate different, alternative parts without leaving the scope of the invention.

Figure 1:
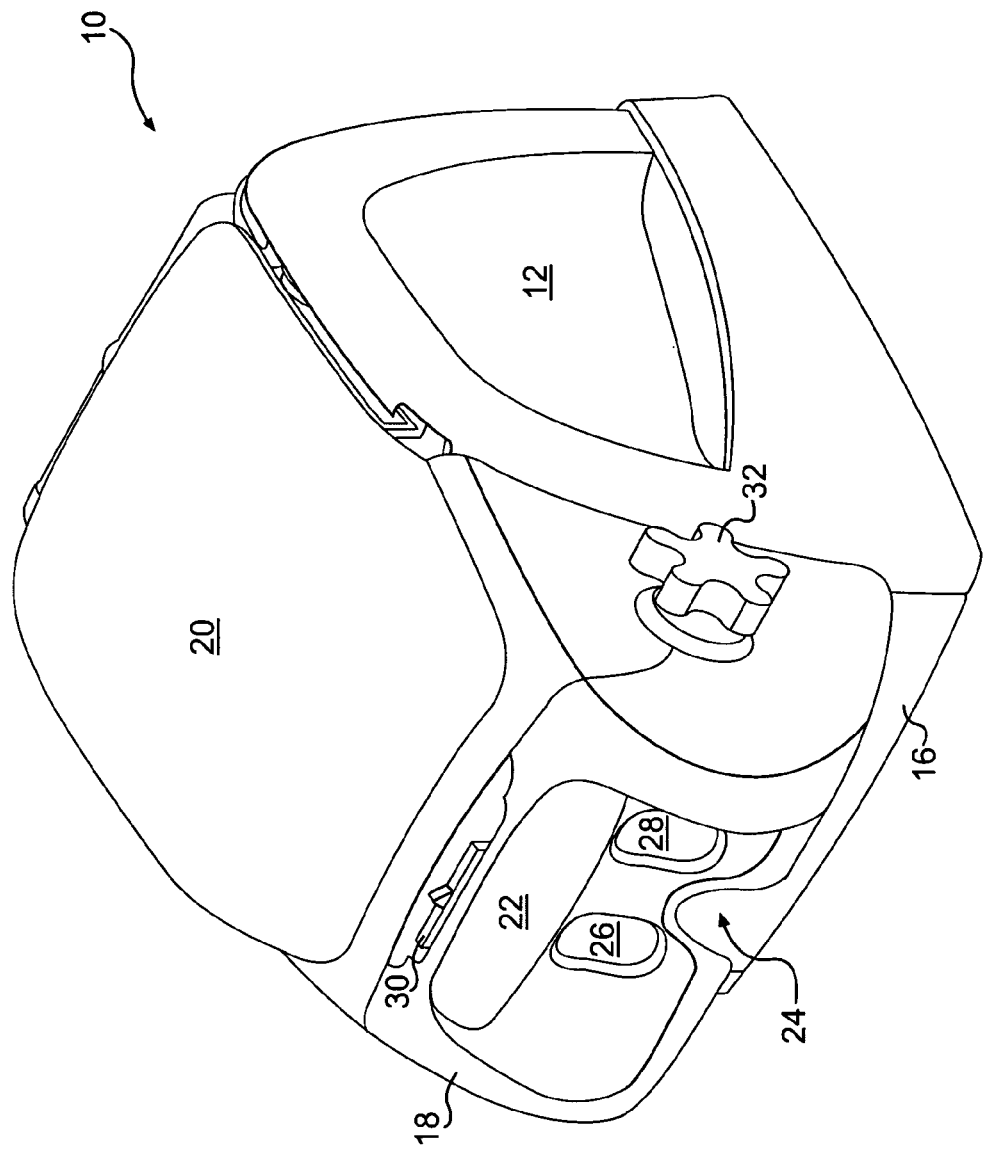
FIG. 1 is a three-quarter front perspective view illustrating a vision testing apparatus in accordance with the present invention.
Figure 2:
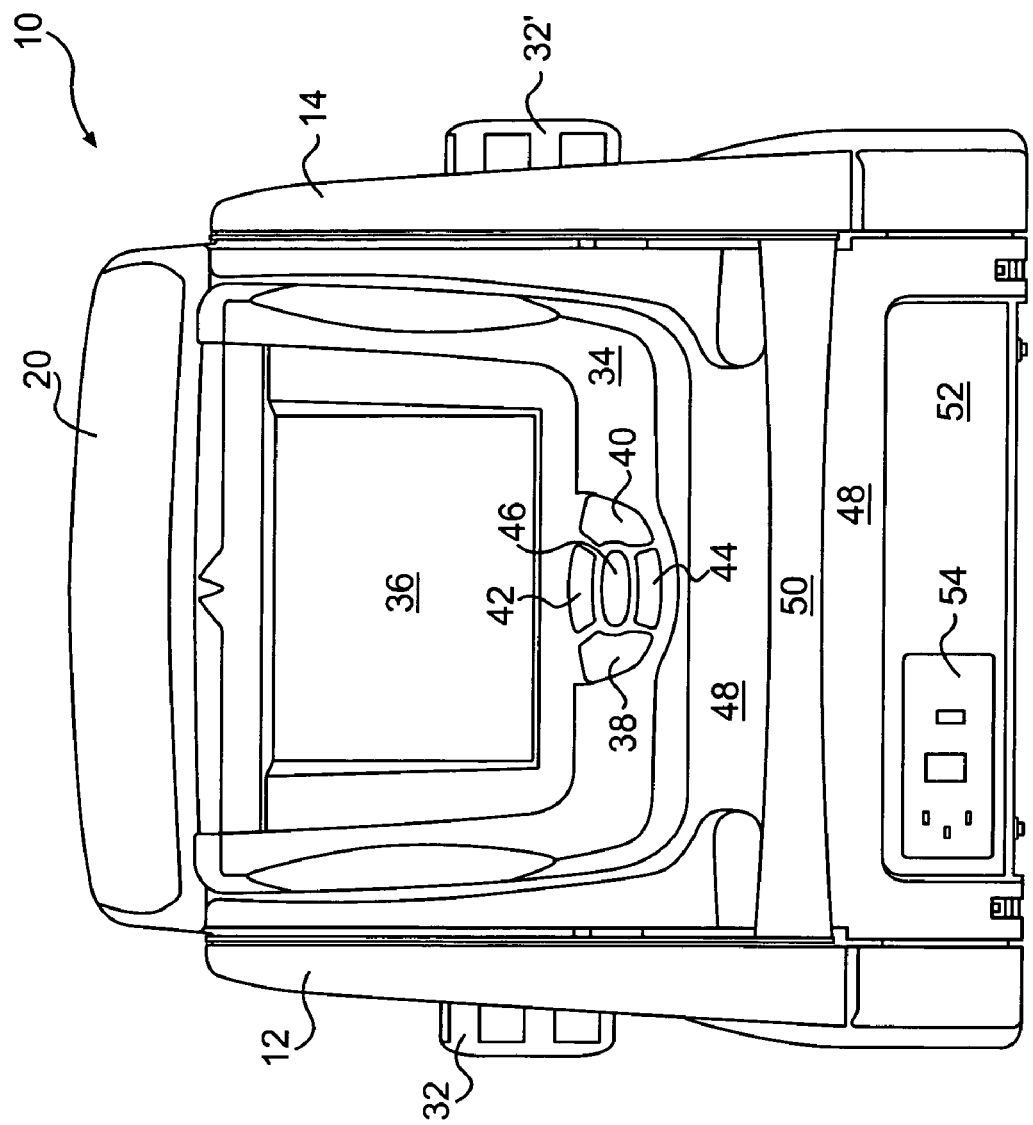
FIG. 2 is rear perspective view of a vision tester including one embodiment of a control board in accordance with the present invention.

Turning now to FIGS. 1 and 2, there is illustrated a vision testing apparatus 10 that is encased by various body panels including a right side cover 12 and a corresponding left side cover 14. A front trim piece 16, a lens cover 18, and a top cover 20 provide an aesthetic quality. Lens cover 18 and top cover 20 are part of a viewer housing 21 described below.

In use, a patient rests their forehead against a headrest 22 with their nose located in or near a nose notch 24. A left front lens and a right front lens 26, 28 are spaced apart to correspond with a patient's left and right eyes. Lenses 26, 28 allow a user to look into a viewing assembly (described below). A slide 30 is mechanically connected to a near/far assembly (described below). A pair of knobs 32, 32' are placed to either side of lens cover 18.

From a rear view perspective, there is illustrated a control board 34. Control boards or remote controls are generally known in the art (see U.S. Pat. No. 4,740,072). Control board 34 of the present invention includes a display screen 36 with left, right, up, and buttons identified as elements 38, 40, 42, and 44. The buttons would be used to navigate control options displayed on screen 36 although the use of a touch sensitive screen, mouse and/or like is also envisioned to control apparatus 10. In one preferred embodiment an optional button 46 could be included for other functions.

As illustrated, control board 34 nests within a back cover 48. Board 34 is selectively held in cover 48 by a rib, groove or other known technique. This facilitates transport of apparatus 10. Board 34 can be removed from the nesting relationship while still remaining in connection or communication with apparatus 10 via a wired or wireless connection. A cross member 50 forms a part of a recessed handle 51 (see FIGS. 11, 12 and 13), and member 50 nests in a recess of back cover 48. An electrical housing 52 contains electrical components such as a fuse and an electrical coupling 54 in order to connect apparatus 10 to a power source via a power cord (not shown).

In a preferred embodiment, the various body panels, knobs, cross members and the like are plastic and are connected to the underlying chassis or apparatus components via known methods and fasteners, such as snap fit connections, bayonet connectors, adhesives, or the like. It is preferred that at least one of the body panels, such a top cover 20, could be easily removed to facilitate maintenance, repairs or service of the underlying components. The chassis is typically a metal or plastic support structure, although it could be formed from any number of materials. It will be apparent to one skilled in the art that the look, design, placement or feel of the various external components can be changed without altering the execution of the present invention. For instance, a fixed, folding, and/or locking handle could be secured to the chassis or body panels for transporting the apparatus. One skilled in the art will also appreciate that various techniques and constructions can be used to encase the components of a vision testing apparatus and provide controls therefore.

Figure 3:
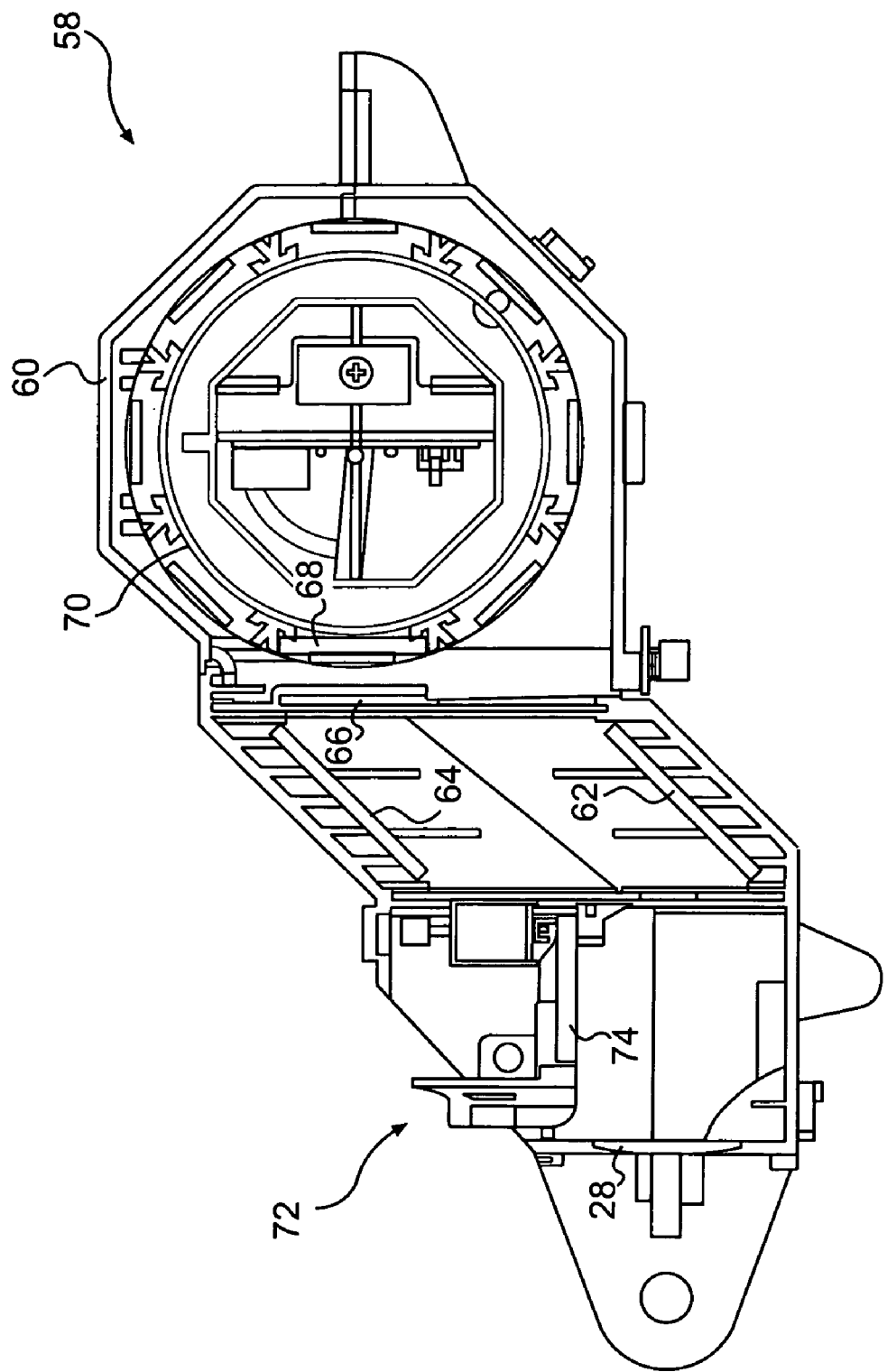
FIG. 3 is a cut-away view of a viewing assembly illustrating an optical path in accordance with the present invention.
Figure 5:
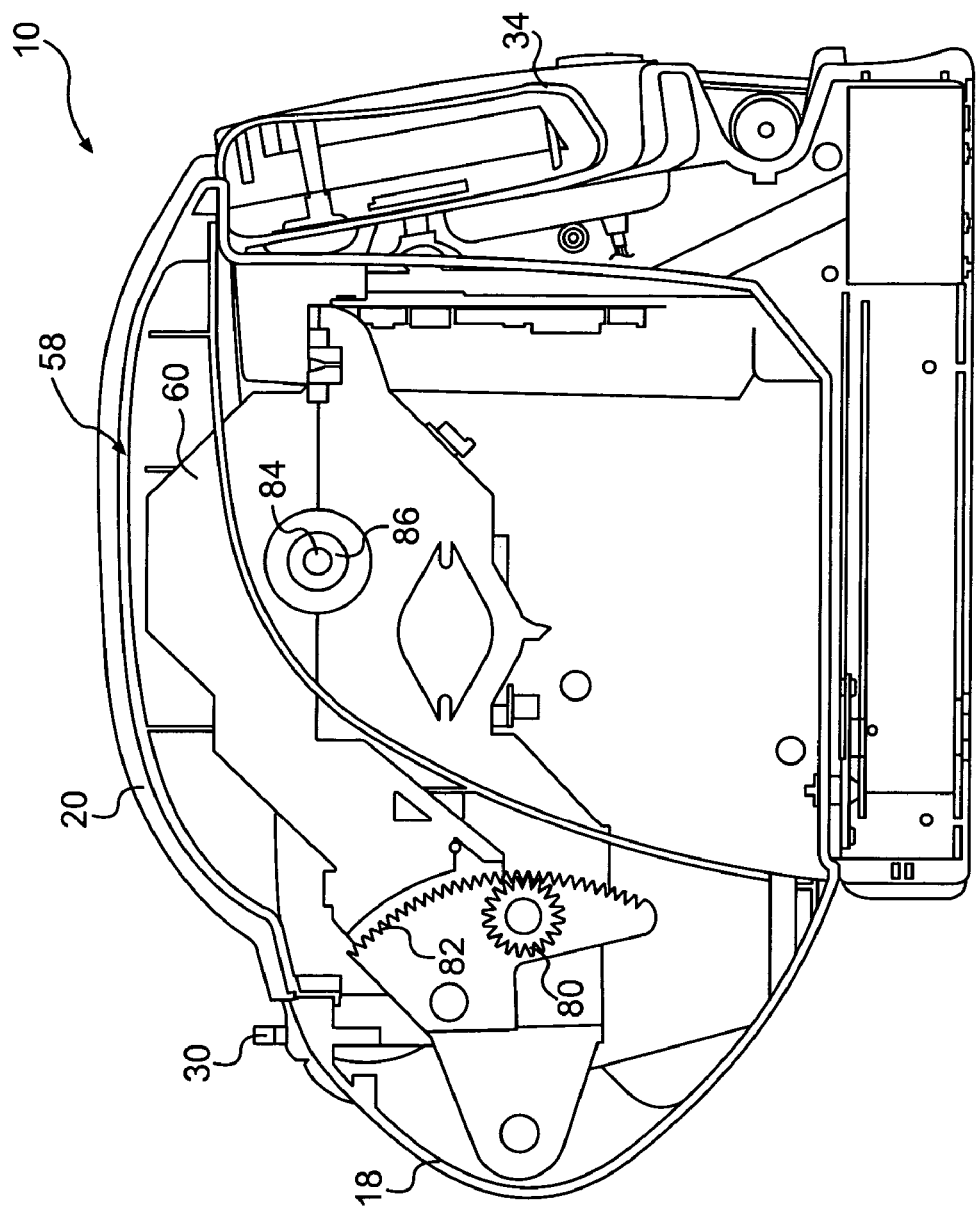
FIG. 5 is a side cut-away view of a vision testing apparatus illustrating a viewing assembly in a far-vision testing position and other components in accordance with the present invention.

FIG. 3 is a right side view of the viewing assembly 58 briefly mentioned above. The viewing assembly includes a light occluding casing 60. Viewing assembly 58 further includes at least one front lens. From this right side perspective, only right lens 28 is illustrated. An optical path (not illustrated) is created from lens 28 to a first mirror 62. The optical path is redirected to a second mirror 64. The second mirror directs the optical path through an optional transparent panel 66 to a test slide 68 mounted on a rotatable drum 70. A drum axle and an axle bearing are illustrated in FIG. 5 at 84 and 86, respectively. Slide 68 is illuminated via a light source behind the slide. Each slide provides an image display via a film secured to or within the slide that presents characters to be viewed by a patient. The drum rotates in order to present different glass slides and, thus, different images to the patient. The patient's view of the image display is generated by testing either their left or right eye or both eyes combined.

In general, it is known in the prior art to include a front lens, a test slide, a light source, and a rotatable drum wherein the test slide creates an image display to be viewed by a patient. The optical path can be a straight line from the lens to the to the image display or it may be redirected by one or more mirrors. The course of the optical path partially depends upon the structure of the viewing assembly. Further elaboration of these known features is not required as one skilled in the art will be familiar with the various configurations and combinations of features required to create an image display in a vision testing apparatus.

Figure 4:
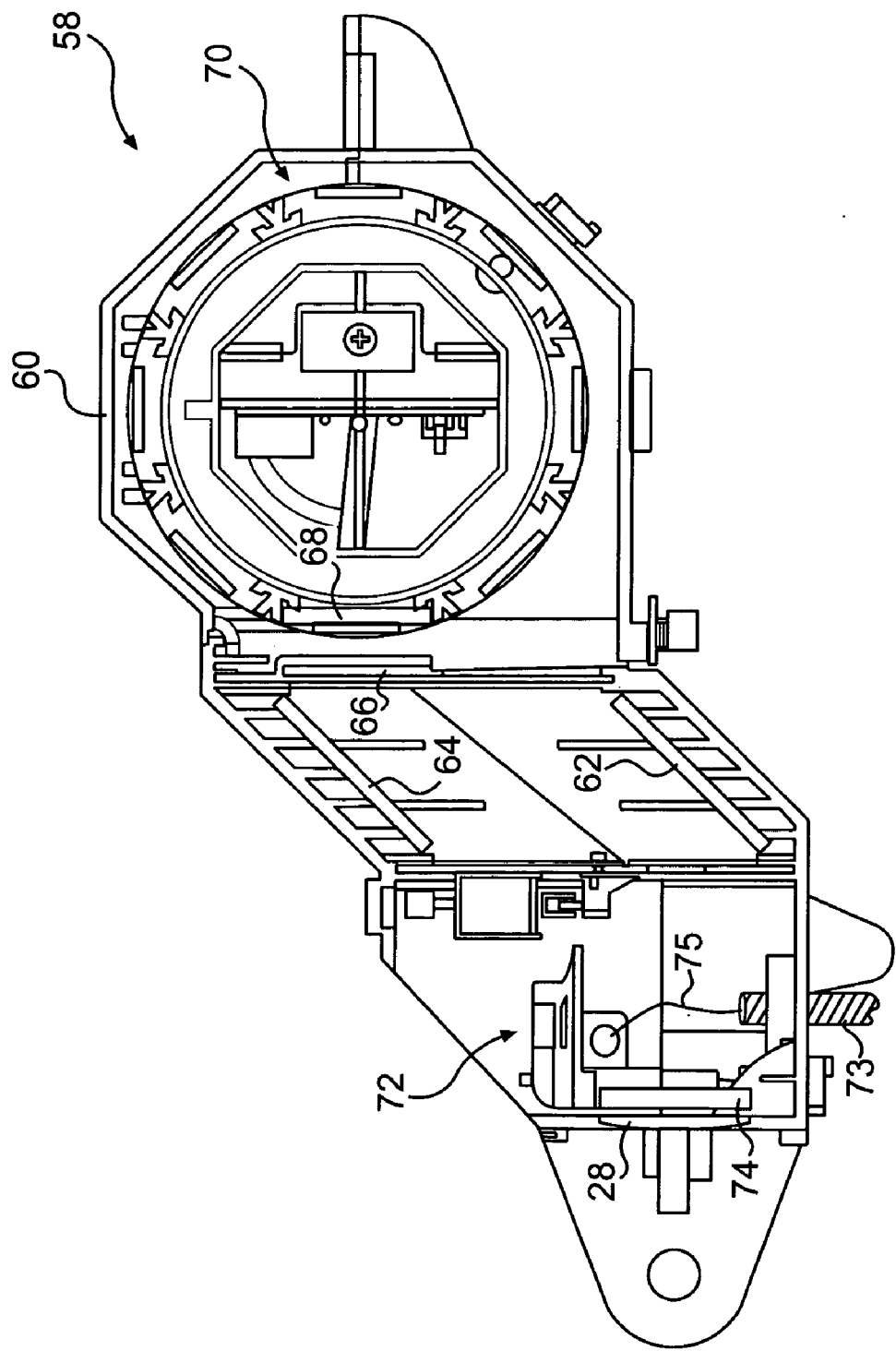
FIG. 4 is a cut-away view of the viewing assembly illustrating an optical path in accordance with the present invention.

Also illustrated in FIGS. 3 and 4 is a near/far assembly 72. Slide 30 is actuated to rotate near/far assembly 72 so as to selectively intersect the optical path between front lenses 26, 28 and test slide 68. A sleeve 73 for a push/pull cable 75 connects near/far assembly 72 and slide 30 (see FIG. 6). Sleeve 73 and/or cable 75 is secured or fastened to slide 30 by a known method such as welding, a clip, adhesive, or the like. Sleeve 73 is secured to the inside of lens cover 18 and to lower section of casing 60. Sleeve 73 enters viewing 58 assembly from the bottom of casing 60.

As illustrated in FIG. 4, cable 75 exits sleeve 73 near assembly 72. Cable 75 is connected to the assembly by known methods, including welding, a clip, adhesive, or the like. Moving slide 30 alternately causes cable 75 to rotate assembly 72 ninety degrees about a pivot point. In FIG. 3, slide 30 has been actuated to rotate near/far assembly 72 so as to not intersect the optical path. Therefore, the simulated distance of the image display from the patient is about twenty feet. This is considered far vision testing, and the patient's line of sight should be roughly straight ahead. The patient attempts to identify characters in the image display in order to test their far vision.

FIG. 4 is the same as FIG. 3, but FIG. 4 illustrates cable 75 having been actuated so as to move a near lens 74 to intersect the optical path. Here, the simulated distance of the test slide from the patient is about 14 inches. For near vision testing, the patient's line of sight should be angled downwards relative to the position of the patient's head. Near and far vision testing is accomplished via one optical path per tested eye.

Turning now to FIG. 5, there is illustrated a cut-away view of apparatus 10 with casing 60 of viewing assembly 58. FIG. 5 illustrates an example of a rotating mechanism for rotating viewing assembly 58 along a defined arc in order to vary a patient's line of sight. Knobs 32, 32' in FIG. 2 correspond to, and are in connection with a pair of cogs. The cogs are located on the right and left side of assembly 58. Only right side cog 80 is illustrated from the perspective of FIG. 5.

Knob 32 is rotated to move cog 80 along a path provided by teeth 82. Each side of the viewing assembly would include the cog and teeth. This rack-and-pinion mechanism allows viewing assembly 58 to be rotated within the body panels and viewer housing 21 of apparatus 10 without changing the height of apparatus 10 or otherwise moving apparatus. Teeth 82 are integrated into casing 60 where casing 60 is plastic. Cog 80 is frictionally but rotatably fit over a post on a viewer support 160 (described below). Lens cover 18 and top cover 20 are joined so as to provide an aperture to connect the knob to the cog. However, one skilled in the art will appreciate that other mechanisms and materials for rotating viewing assembly 58 independently of apparatus 10 and forming casing 60 could be utilized.

From this right side perspective, knob 32 is rotated counter-clockwise to lift assembly 58 upwards and vice-versa. This places assembly 58 in the far vision testing position as the patient looking substantially straight ahead would have a line of sight essentially perpendicular to the front lenses.

Figure 6:
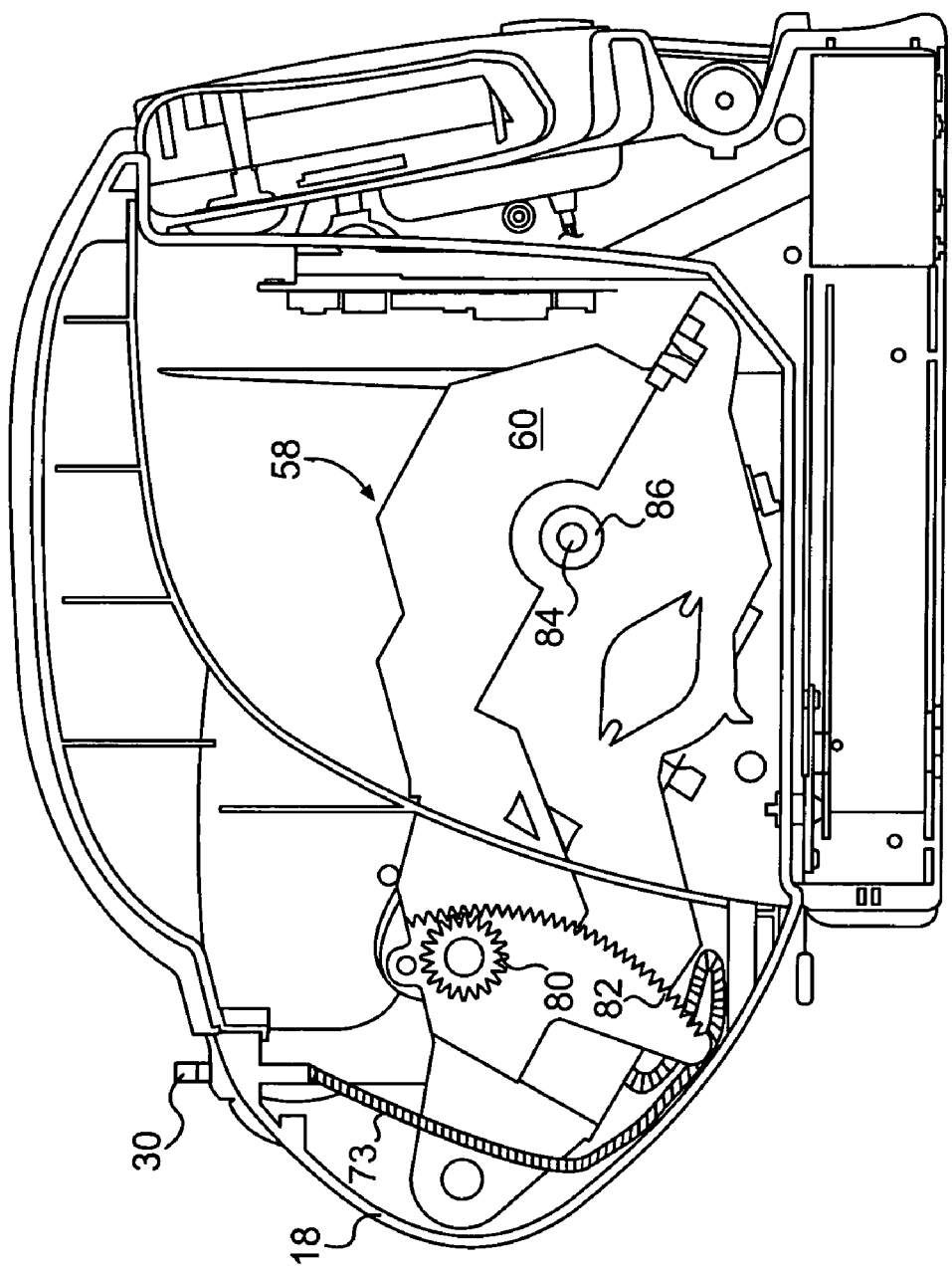
FIG. 6 is a side cut-away view of a vision testing apparatus illustrating a viewing assembly in a near-vision testing position and other components in accordance with the present invention.

FIG. 6 also presents a cut-away right side view. Here, viewing assembly 58 has been lowered to a near vision testing position. As shown, the frame and outer panels do not move between far vision testing (FIG. 5) and near vision testing (FIG. 6). Forehead rest 22 does not move so the patient must angle their line of sight to a downward direction in order to view the image display via the optical path. While providing a lone optical path, apparatus 10 of the present invention accurately mimics natural lines of sight for near and far vision testing. The specific downward angle of viewing assembly 58 with respect to the front lenses can be varied by a patient to find a comfortable angle for near vision testing. Common near vision line of sight angles are about negative twenty degrees to negative thirty degrees relative to a straight-ahead line of sight. The appropriate angle will vary from patient to patient, particularly for those patients with corrective lens. In a preferred embodiment, the pivot range for the viewing assembly 58 is about 0 (straight line) to −30 degrees (i.e., a 30 degree downward angle from a straight line of sight).

Figure 7:
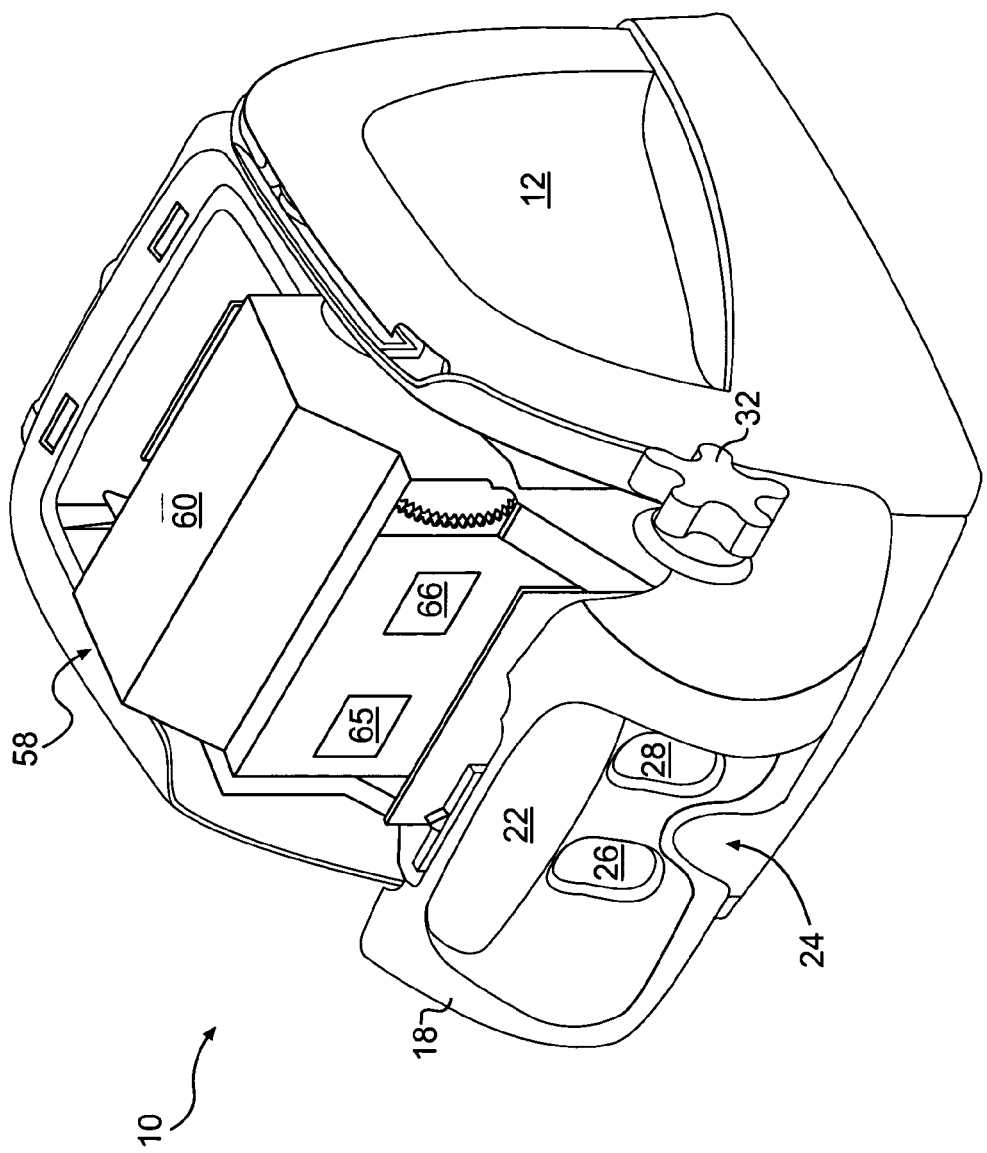
FIG. 7 is a perspective view wherein portions of the viewing assembly and plastic housing are removed to illustrate the inside of a viewing assembly in accordance with the present invention.

In a preferred embodiment, apparatus 10, and specifically viewing assembly 58, includes a pair of transparent panels 65, 66 intersecting the optical path between left lens 26, right lens 28 and test slide 70, as illustrated in FIG. 7. Top panel 20, portions of casing 60, and certain aspects of assembly 58 are deleted in this view to facilitate the understanding of the invention.

Panels 65, 66 are, in a preferred embodiment, liquid crystal displays (LCDs) that allow light to pass through the plane of the panels in an unactivated state. Panels 65,66 include a grid or arrangement of pixels with at least one pixel corresponding to each character on test slide 70. Using known techniques, the pixels can be individually activated. In an activated state, the pixels shade, obscure, or otherwise block the patient's view of the corresponding character in the image display. One skilled in the art will appreciate that other types of panels are, or will be, available to accomplish this feature of the invention.

Figure 8:
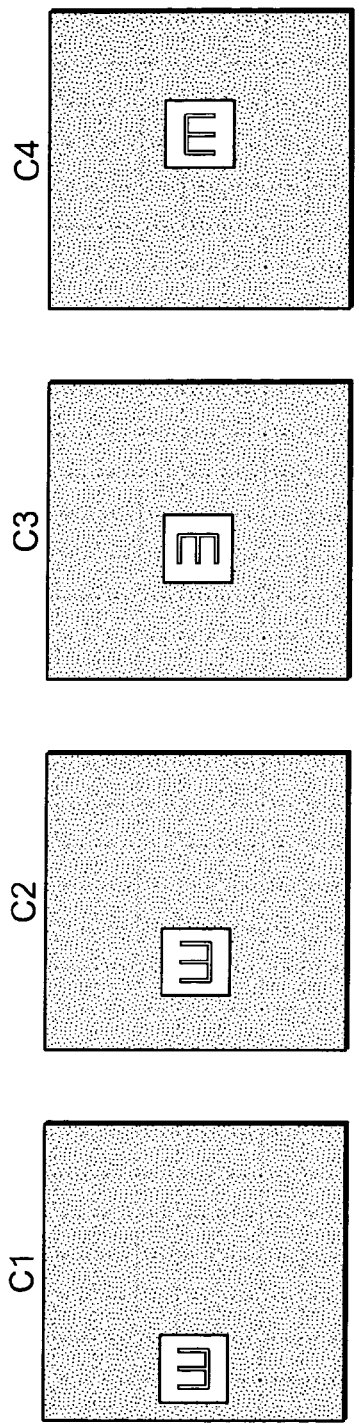
FIG. 8 C1-C4 are schematic views of an image display wherein certain objects are obscured so that a single character is isolated in accordance with the present invention.
Figure 9:
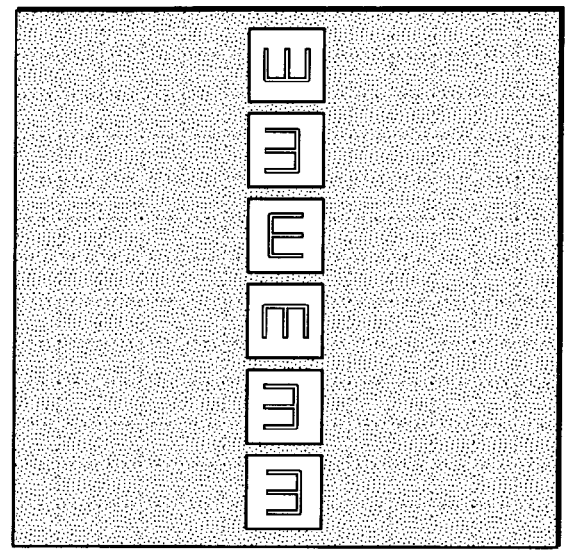
FIG. 9 illustrates an image display in accordance with the present invention.

Turning to FIG. 8 C1-C4 and FIG. 9, there are illustrated representative views of a patient's perception of the image display with portions of the test sample obscured by pixels activated on panels 65, 66. FIG. 8 C1-C4 illustrate the capability of highlighting individual characters. A row of test characters from the display image are visible in FIG. 9. As discussed above, it is also envisioned that the activated pixels may only obscure or shade the test characters, as opposed to blocking the characters entirely. These views are only representative as it may be possible to see the borders delineating each pixel from any adjacent pixel. In other words, the actual perception of the test image will vary depending on the mode of accomplishing this aspect of the invention.

Figure 10:
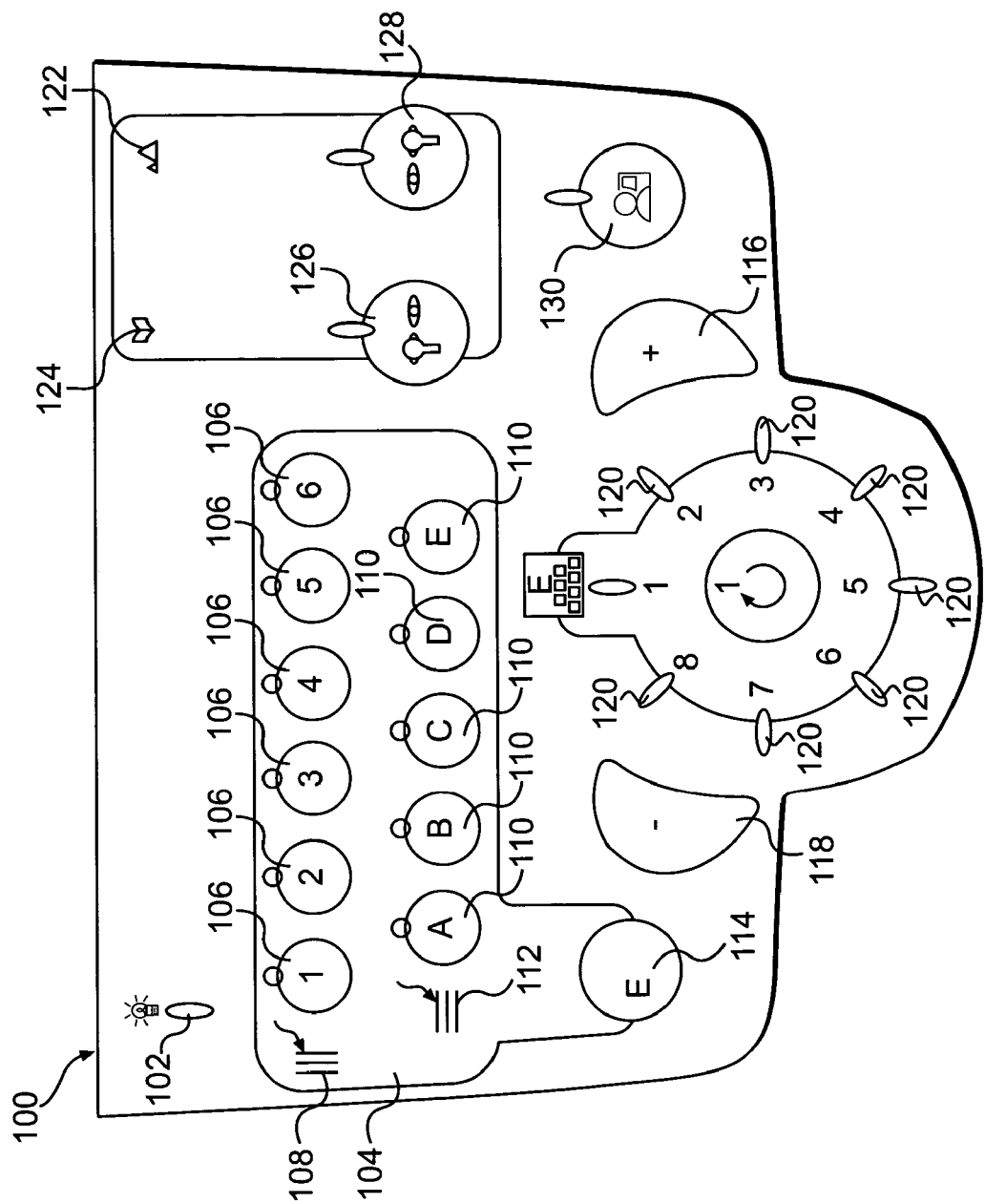
FIG. 10 is a view of one preferred control board in accordance with the present invention.

FIG. 10 illustrates another preferred embodiment of a control board 100. A power indicator 102 is illuminated when apparatus 10 is turned on for use. A selector panel 104 includes two rows of buttons. A row of column buttons 106 beside a column indicia 108 illuminate or include an adjacent light to indicate which columns are visible in the image display. The tester can individually toggle each column 'on' or 'off' to block or otherwise obscure the selected column in the 'off' position. Likewise, a plurality of row buttons 110 beside a row indicia 112 illuminate or include an adjacent light to indicate which rows are visible or unobscured in the image display. A reset button 114 toggles the image display between all rows and columns unobscured and the top row of the image display unobscured with the other rows obscured. In the latter mode, the tester then able to designate which rows are visible for testing. Actuating the column buttons toggles the visibility of the characters in the visible row (or rows) and that column (or columns). Rotatable drum 68 is advanced via plus and minus buttons 116, 118. The visible test slide is indicated to the tester via selection lights 120.

Control board 100 includes additional apparatus status information. A far indicator 122 includes an associated light to inform the tester when the near/far assembly has been placed in the far vision testing position. Likewise, a near indicator 124 is illuminated via backlighting or a separate light during near vision testing. A sensor (not shown) detects the position of near/far assembly 72 and the sensor is in electrical connection with the lights at indicators 122, 124. A left selector 126 and right selector 128 can be selectively actuated to close shutters (not shown) behind the left and right lens 26, 28. Again, lights are included with selectors 126, 128 to apprise the tester of the status of apparatus 10. Finally, at least one head position sensor (not shown) selectively activates a light at indicator 130. If the patient has not properly positioned their head for vision testing, the head position sensor deactivates the light at indicator 130.

Control board 100 is one preferred embodiment of a control board or remote control in accordance with the present invention. The look and feel of the control board are arbitrary and the board merely needs to function to control the features of apparatus 10. One skilled in the art will appreciate that additional features and controls could be added to board 100 or that existing features could be removed. For instance, it is possible for the tester to manually close shutters associated with the left and right front lenses to block the optical path to one or both of a patient's eye(s).

Figure 11:
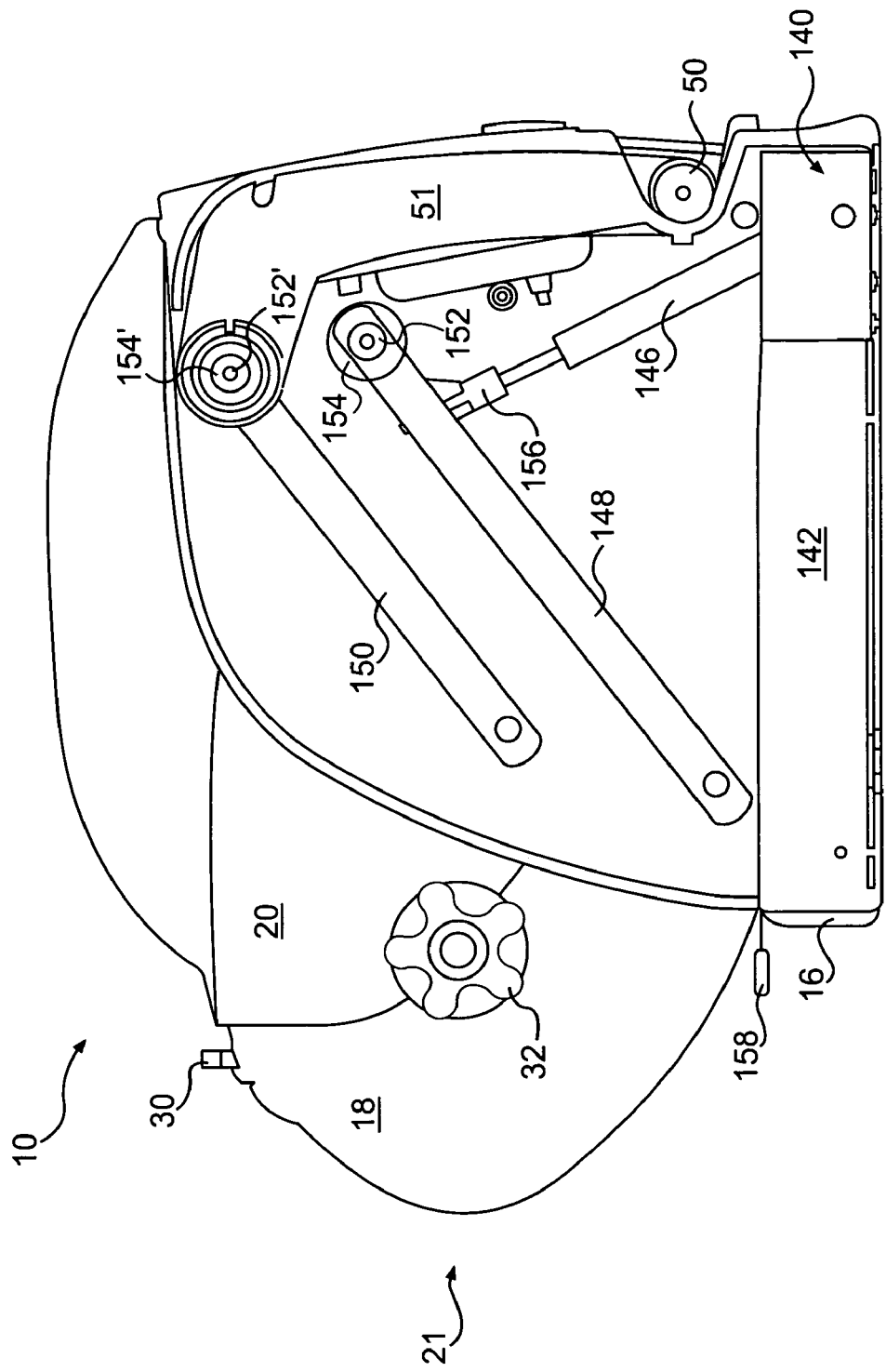
FIG. 11 is a cut-away side view of a vision testing apparatus in a storage/transport configuration in accordance with the present invention.

With right side cover 12 removed, FIG. 11 illustrates a chassis 140 with a base 142 riveted or otherwise secured to a sidewall. The sidewall is illustrated as being transparent in order to illustrate the mechanism behind it. The sidewall is, in a preferred embodiment, basically a flat metal panel that serves as a part of the chassis or frame. A second sidewall would be provided on the left side of the apparatus. The components secured a sidewall, including the components of a lifting mechanism as described below, are duplicated on the left side of apparatus 10 in a mirrored relationship.

A lifting mechanism consists of a gas spring 146 and two unequal length, non-parallel arms 148, 150. Arms 148, 150 are mounted on axles 152, 152'. Axles 152, 152' are secured to the bearings 154, 154', respectively, which are mounted in a sidewall by known methods. The distal ends of arms 148, 150 are bearing mounted over posts. A counterbalancing linear gas spring 146 is secured to lower arm 148 by a pin 156 that passes through apertures in lower arm 148. Gas spring 146 is operable to rotate arms 148, 150 in the opposite rotational direction to the couple produced by the weight of viewer housing 21. Upper arm 150 is secured to the sidewall in part by a friction washer that provides a adjustment for the counterbalancing force. On skilled in the art will appreciate that mechanical springs, hydraulic pistons, or other equivalents could be used to counterbalance the weight of housing 21.

FIG. 11 illustrates a storage or transport configuration where viewer housing 21 is lowered until it is essentially in contact with base 142. A spring assisted catch lock 158 engages housing 21 to secure it in this storage configuration. The tester or patient actuates lock level 158 to release housing 21 from base 142. Various methods for mechanically latching housing 21 to base 142 are available. Apparatus 10 operates in this storage/transport position in order to test young children or any short patient.

Base 142 could be used to store small articles. The storage compartment (not illustrated) could be a sliding drawer, removable bin, or the like. This storage compartment would also include a latching mechanism to prevent the compartment from unexpectedly opening. Handle 51 is recessed behind the sidewalls on either side of apparatus 10 but is frictionally fit and rotatable about bearing 154' or axle' 152'. Cross member 50 of handle 51 can be raised into a position to facilitate transporting apparatus 10.

Figure 12:
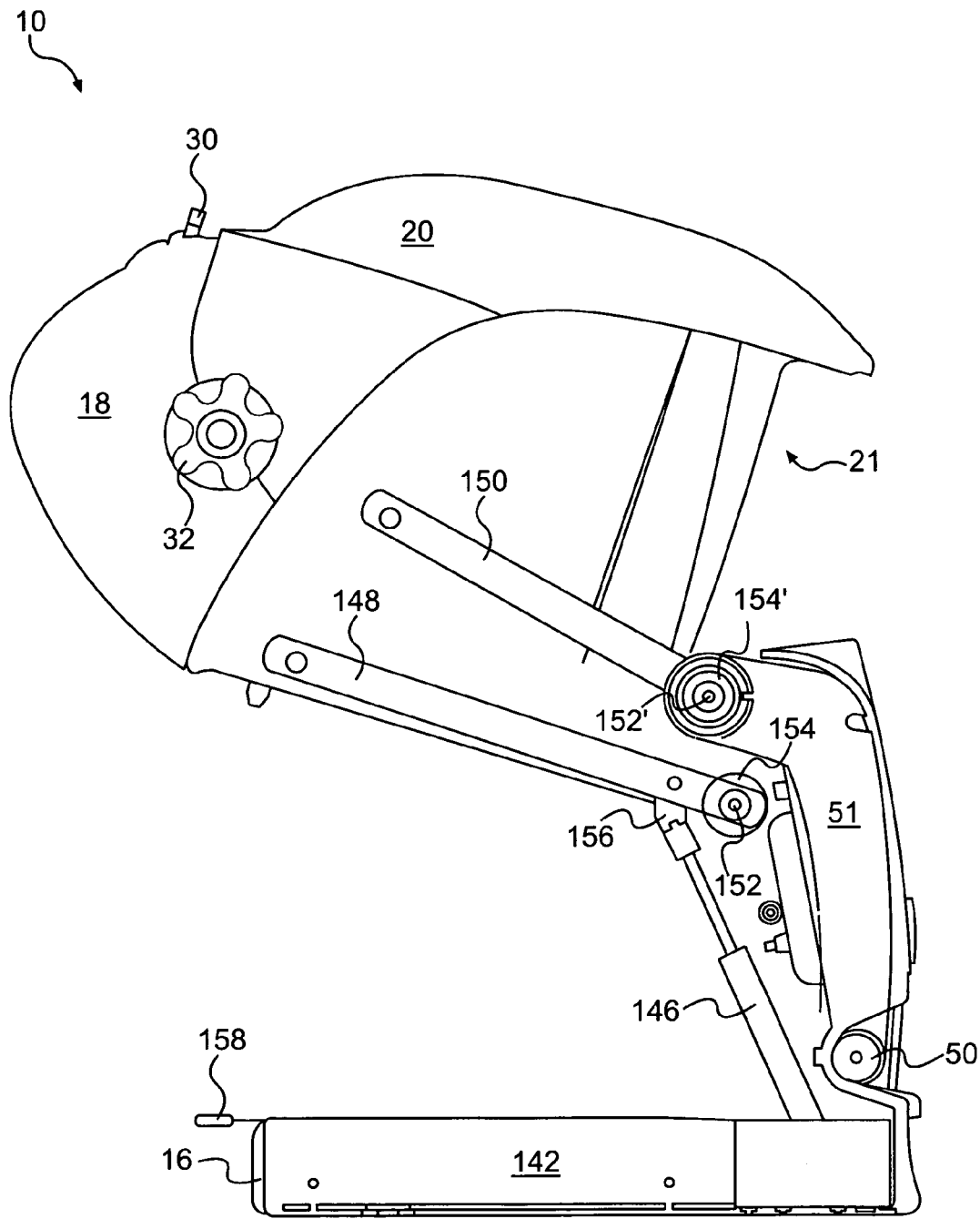
FIG. 12 is a cut-away side view of a vision testing apparatus in one position of a range of raised configurations in accordance with the present invention.

In use, the lifting mechanism operates to place housing 21 in a range of raised configurations. Lower arm 148 and upper arm 150 are not equal in length and are not parallel. The multi-link geometry acts as a lost motion coupling between chassis 140 and housing 21, which is to say that the arms control the locus of the viewing assembly through a near vertical path. The lost motion mechanism keeps the fronts lenses in housing 21 nearly perpendicular to base 142 when assembly 58 is in a far vision testing position. A patient then has a substantially straight line of sight during testing whether the viewer housing is in the storage configuration or most raised configurations so long as assembly is in the far vision testing position. Near the highest raised positions, as shown in FIG. 12, housing 21 begins to tilt. An extremely tall patient would have to lean forward to maintain the straight line of sight.

Figure 13:
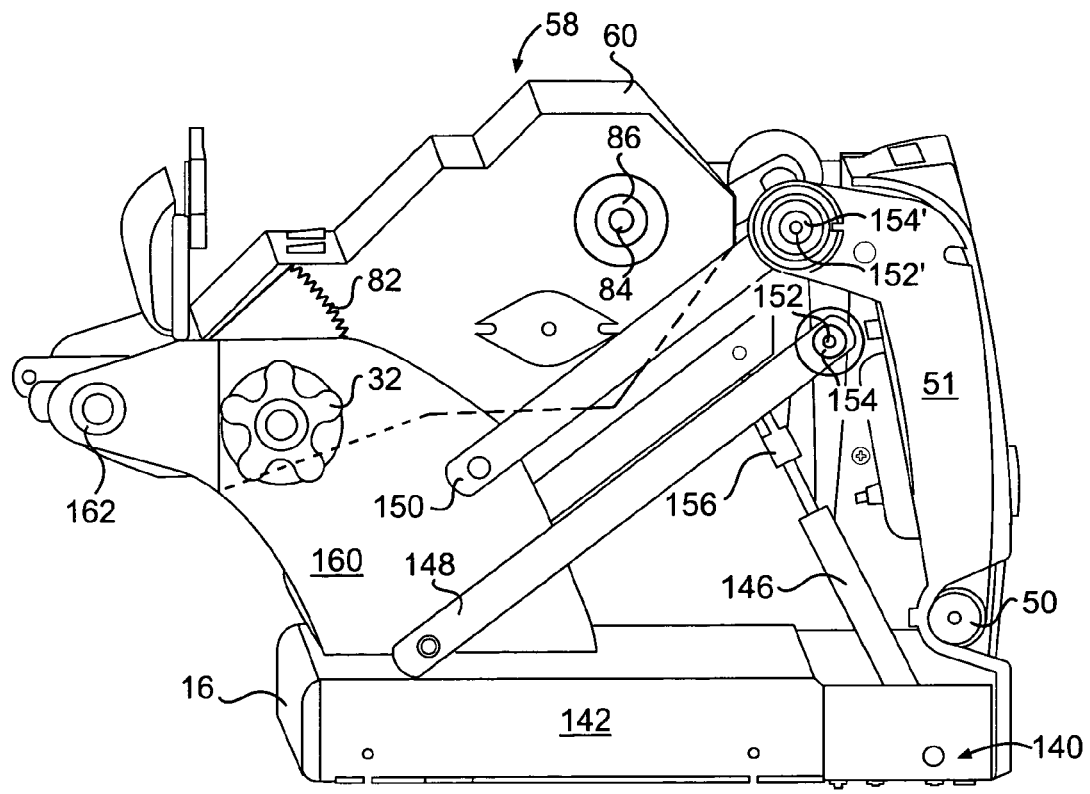
FIG. 13 is a cut-away side view illustrating the interior of a viewer housing in accordance with the present invention.

Viewer housing and exterior body panels are removed in FIG. 13. A viewer support 160 provides the posts to which arms 148 and 150 are frictionally but rotatably fit. Casing 60 includes a pair of support posts on either side of viewing assembly 60. Support post 162 frictionally fits with an aperture in support 160. Assembly 58 may or may not rotate slightly in relation to support 160 as the lifting mechanism raises or lowers the housing 21. However, viewing assembly 58 does rotate relative to chassis 140, base, 142, and arms 148, 150 when knob 32 is rotated. The rack-and-pinion mechanism rotates assembly 58 around post 162. One skilled in the art will appreciate that there are additional constructions available to lift a viewing assembly of a vision testing apparatus without departing from the scope of the invention as claimed below.

That which has been described above is a compact vision testing apparatus with height and line of sight adjustments to serve a wide variety of test subjects, and with a wide variety of test functions, including the ability to at least partially obscure an image display. While the invention has been described in connection with what is presently considered to be the best practice and preferred embodiments, it is to be understood that the invention is not limited to the disclosed embodiment, but, on the contrary, is intended to cover various modifications and equivalent arrangements included within the spirit and scope of the appended claims, which scope is to be accorded the broadest interpretation so as to encompass all such modifications and equivalent structures.

What is claimed is:

1. A vision test apparatus comprising:
   a chassis;
   a viewing assembly comprising a light occluding casing supported by said chassis, said viewing assembly including at least one front lens and an image display, said viewing assembly creating an optical path within said light occluding casing from said at least one front lens to said image display; and
   a rotating mechanism operable to rotate said viewing assembly relative to a patient independently of adjusting the height of the viewing assembly relative to a patient, said mechanism operable to adjust a patient's line of sight into said at least one front lens.

2. The apparatus of claim 1, wherein said mechanism comprises a rack-and-pinion mechanism.

3. The apparatus of claim 1 wherein said at least one front lens comprises a left lens and a right lens, said left and right lenses lens are selectively operated alone or in combination.

4. The apparatus of claim 1 further comprising a near/far assembly selectively operable to create at least two virtual visual distances from the patient to said image display.

5. The apparatus of claim 4, wherein said near/far assembly selectively creates virtual visual distances using a lone optical path.

6. The apparatus of claim 1, further comprising a lifting mechanism connecting said chassis and said viewing assembly, wherein said lifting mechanism is operable to place said viewing assembly at various positions relative to said chassis.

7. The apparatus of claim 6, wherein said lifting mechanism comprises a lost motion coupling.

8. The apparatus of claim 7, wherein said lifting mechanism further comprises a gas spring to facilitate the operation of said lifting mechanism.

9. The apparatus of claim 1, wherein said viewing assembly further comprises at least one transparent panel intersecting said optical path, said at least one panel selectively operable to obscure at least a portion of said image display.

10. A vision testing apparatus comprising:
    a viewing assembly including a front lens and an image display;
    an optical path created by said viewing assembly, said optical path optically connecting said image display to said front lens;
    a transparent panel intersecting said optical path, said transparent panel comprising a plurality of separately operable pixels; and
    whereby said transparent panel is selectively operable to obscure at least a portion of said image display.

11. The apparatus of claim 10, further comprising a control board to selectively activate at least one pixel of said transparent panel.

12. The apparatus of claim 11, wherein said transparent panel is a liquid crystal display panel.

13. The apparatus according to claim 12, further comprising a control board for controlling said selectively activated pixels of said LCD panel in order to highlight or isolate characters presented in said image display to a patient.

14. The apparatus of claim 10, further comprising a rotating mechanism operable to rotate said viewing assembly relative to a patient.

15. The apparatus of claim 14, wherein said rotating mechanism comprises a rack-and-pinion mechanism.

16. The apparatus of claim 15, wherein said near/far assembly selectively creates virtual visual distances using a lone optical path.

17. The apparatus of claim 16, wherein said virtual visual distances simulate distances from said front lens to said image display from about 14 inches to about 20 feet.

18. The apparatus of claim 10, further comprising a near/far assembly to create at least two virtual visual distances from a patient to said image.

19. The apparatus of claim 10, further comprising a chassis to support said viewing assembly and a lifting mechanism connecting said chassis to said viewing assembly, wherein said lifting mechanism is operable to place said viewing assembly at various positions relative to said chassis.

20. The apparatus of claim 19, wherein said lifting mechanism comprises a lost motion coupling and a gas spring to facilitate the operation of said lifting mechanism.

21. A vision test apparatus comprising:
    a viewing assembly, said viewing assembly including an image display and at least one front lens, said viewing assembly providing an optical path from said image display to said at least one front lens;
    a chassis including a base and sidewalls;
    a lifting mechanism, said lifting mechanism connecting said chassis to said viewing assembly; and wherein said lifting mechanism is selectively operable to raise and lower said viewing assembly along a substantially vertical path relative to said base.

22. The apparatus of claim 21, wherein said lifting mechanism comprises a lost motion coupling.

23. The apparatus of claim 22, wherein said lifting mechanism further comprises a gas spring.

24. The apparatus of claim 21, further comprising a rotating mechanism operable to rotate said viewing assembly relative to a patient independently of adjusting said lifting mechanism.

25. The apparatus of claim 24, wherein said rotating mechanism comprises a rack-and-pinion mechanism.

26. The apparatus of claim 21, further comprising a near/far assembly selectively operable to create virtual visual distances from said front lens to said image display via said optical path.

27. A vision test apparatus comprising:
a viewing assembly with a light-occluding casing,
a front lens for viewing the interior of said casing,
an image display created inside said casing,
an optical path between said front lens and said image display,
a transparent panel intersecting said optical path, said transparent panel including a plurality of selectively activated pixels,
a control board controlling said transparent panel to selectively isolate a portion of said image display,
a secondary lens moveable to selectively intersect said optical path wherein the front lens and said secondary lens are operable to create virtual visual distances from said front lens to said image display; and
wherein said viewing assembly is rotatable relative to a patient.

28. A vision test apparatus comprising:
a chassis;
a viewing assembly supported by said chassis, the viewing assembly including a light-occluding casing,
a front lens for viewing the interior of said casing,
an image display created inside said casing,
an optical path between said front lens and said image display,
a secondary lens moveable to selectively intersect said optical path wherein the front lens and said secondary lens are operable to create virtual visual distances from said front lens to said image display,
a lifting mechanism connecting said chassis and said viewing assembly; and
wherein said lifting mechanism is operable to place said viewing assembly at various positions relative to said chassis, said lifting mechanism moves said viewing assembly through a substantially vertical path.

* * * * *